(12) United States Patent
Cao et al.

(10) Patent No.: US 7,498,011 B2
(45) Date of Patent: Mar. 3, 2009

(54) ALUMINOPHOSPHATE MOLECULAR SIEVE, ITS SYNTHESIS AND USE

(75) Inventors: Guang Cao, Branchburg, NJ (US); Matu J. Shah, Hackettstown, NJ (US); John F. Brody, Bound Brook, NJ (US); Douglas Lewis Dorset, Milford, NJ (US); Karl G. Strohmaier, Port Murray, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 686 days.

(21) Appl. No.: 11/231,677

(22) Filed: Sep. 21, 2005

(65) Prior Publication Data
US 2006/0074267 A1    Apr. 6, 2006

Related U.S. Application Data

(60) Provisional application No. 60/615,111, filed on Oct. 1, 2004.

(51) Int. Cl.
    *C01B 39/54*    (2006.01)
    *B01J 27/18*    (2006.01)
    *B01J 27/182*    (2006.01)
    *C07C 1/20*    (2006.01)

(52) U.S. Cl. ................ 423/305; 423/306; 502/208; 502/214; 585/640

(58) Field of Classification Search ........... 423/305, 423/306, DIG. 30; 502/208, 214; 585/640
See application file for complete search history.

(56) References Cited

U.S. PATENT DOCUMENTS

| | | | |
|---|---|---|---|
| 6,680,278 B2 | 1/2004 | Cao et al. | |
| 6,914,030 B2 * | 7/2005 | Cao et al. | 502/214 |
| 6,927,187 B2 * | 8/2005 | Cao et al. | 502/214 |
| 6,936,566 B2 * | 8/2005 | Mees et al. | 502/214 |
| 7,247,287 B2 * | 7/2007 | Cao et al. | 423/306 |
| 2003/0231999 A1 | 12/2003 | Cao et al. | |
| 2003/0232718 A1 | 12/2003 | Cao et al. | |

FOREIGN PATENT DOCUMENTS

| | | |
|---|---|---|
| EP | 0 337 479 | 7/1992 |
| EP | 0 324 082 | 8/1992 |

OTHER PUBLICATIONS

Database of Zeolite Structure, Accessed Sep. 30, 2008, 4 pages.*
*Atlas of Zeolite Framework Types*, 5th Edition, Elsevier, London, England (2001).
*SSZ-51—A New Aluminophosphate Zeotype: Synthesis, Crystal Structure, NMR, and Dehydration Properties*, published on the Web by the American Chemical Society on Jun. 23, 2004, Morris et al.

(Continued)

*Primary Examiner*—David M Brunsman (57) ABSTRACT

A large pore (metallo)aluminophosphate molecular sieve is disclosed. The material has an X-ray diffraction pattern including the lines listed in Table 4 and is synthesized in the presence of 4-dimethylaminopyridine as structure directing agent.

27 Claims, 6 Drawing Sheets

XRDs of Samples A, C, & D

OTHER PUBLICATIONS

Van Bekkum et al., *Introduction to Zeolite Science and Practice*, Second Completely Revised and Expanded Edition, vol. 137, pp. 1-67, Elsevier Science, B.V. Amsterdam, Netherlands (2001).

Abstract Translation of Chemical Journal of Chinese Universities, vol. 22, No. 10, pp. 192-195, dated Oct. 2001.

Noble et al., "Microporous Magnesium Aluminophosphate STA-1: Synthesis with a Rationally Designed Template and Structure Elucidation by Microcrystal Diffraction," Angew, Chem. Int. Ed., Engl. 1997, vol. 36, Iss. 1/2, pp. 81-83.

* cited by examiner

Figure 1

Figure 2. XRD's of Example 1 Products

Figure 3. Comparison of Samples A & B

Figure 4. SEM Micrograph of Samples A & B

Sample A					Sample B

Figure 5. XRDs of Samples A, C, & D

Figure 6. XRDs of Calcined Samples A, C, & D

Figure 7. XRDs of Sample C Undergoing A Series of Calcination, Hydration, and Dehydration Treatments Figure 8. XRD Patterns of Example 8

ALUMINOPHOSPHATE MOLECULAR SIEVE, ITS SYNTHESIS AND USE

CROSS REFERENCE TO RELATED APPLICATION

This application claims priority to U.S. Provisional Patent Application No. 60/615,111, filed Oct. 1, 2004.

FIELD

This invention relates to a large pore aluminophosphate molecular sieve, or a substituted derivative thereof, to a method of its synthesis in a low fluoride or fluoride-free medium and to its use in organic conversion reactions.

BACKGROUND

Crystalline molecular sieves have a 3-dimensional, four-connected framework structure of corner-sharing [$TO_4$] tetrahedra, where T is any tetrahedrally coordinated cation. Among the known forms of molecular sieve are aluminosilicates, which contain a three-dimensional microporous crystal framework structure of [$SiO_4$] and [$AlO_4$] corner sharing tetrahedral units, aluminophosphates (ALPOs), in which the framework structure is composed of [$AlO_4$] and [$PO_4$] corner sharing tetrahedral units and silicoaluminophosphates (SAPOs), in which the framework structure is composed of [$SiO_4$], [$AlO_4$] and [$PO_4$] corner sharing tetrahedral units.

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types,* 5th edition, Elsevier, London, England (2001), which is herein fully incorporated by reference.

Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1-67, Elsevier Science, B. V., Amsterdam, Netherlands (2001).

In general, molecular sieves can be divided into small, medium and large pore materials. Thus small pore molecular sieves typically have pores defined by a ring of no more than 8 T atoms and have an average pore size less than about 0.5 nm (5 Å). Medium pore molecular sieves typically have pores defined by a ring of 10 T atoms and have an average pore size about 0.5 to 0.6 nm (5 to 6 Å), whereas large pore materials have pores defined by rings of 12 or more T atoms and a pore size greater than 0.6 nm (6 Å).

Crystalline molecular sieves, as exemplified by zeolites and (metallo)aluminophosphates, are commercially important materials for petroleum processing and petrochemical applications. Because each unique structure type offers new potential for applications in catalysis and separations, there has been sustained research effort, both in industry and academia, for their discovery.

Many molecular sieves are synthesized in the presence of an organic directing agent, such as an organic nitrogen compound. For example, it is known from, for example, U.S. Pat. No. 6,680,278 that a crystalline silicoaluminophosphate molecular sieve of the CHA framework type (a small pore material), can be synthesized in the presence of an organic directing agent mixture comprising tetraethylammonium cations and one or more dimethylamino moieties selected from one or more of N,N-dimethylethanolamine, N,N-dimethylpropanolamine, N,N-dimethylbutanolamine, N,N-dimethylheptanolamine, N,N-dimethylhexanolamine, N,N-dimethylethylenediamine, N,N-dimethylbutylenediamine, N,N-dimethylheptylenediamine, N,N-dimethylhexylenediamine 1-dimethylamino-2-propanol, N,N-dimethylethylamine, N,N-dimethylpropylamine, N,N-dimethylpentylamine, , N,N-dimethylhexylamine and N,N-dimethylheptylamine. Other organic directing agents that have been used in the synthesis of CHA framework type materials include isopropylamine or di-n-propylamine triethylamine, cyclohexylamine, 1-methylamidazole, morpholine, pyridine, piperidine, diethylethanolamine, and N,N,N',N'-tetraethylethylene diamine.

It is also known to use fluoride-containing compounds, such as hydrogen fluoride, as mineralizing agents in molecular sieve synthesis. For example, EP-A-337,479 discloses the use of hydrogen fluoride in water at low pH to mineralize silica in glass for the synthesis of ZSM-5. In addition, U.S. Patent Application Publication No. 2003/0231999 published Dec. 18, 2003 and incorporated herein by reference, discloses that aluminophosphate or silicoaluminophosphate molecular sieves having the CHA framework type can be synthesized in the presence of fluoride ions using the dimethylamino compounds disclosed in U.S. Pat. No. 6,680,278 as directing agents. However, fluoride-based syntheses pose environmental problems in that they use hydrogen fluoride in the synthesis medium and/or produce hydrogen fluoride on calcination to remove the organic directing agent from the molecular sieve product.

Currently, an entirely rational approach that leads to the synthesis of unique framework materials is not available, due to the fact that all crystalline microporous materials are metastable phases and they are kinetic products. Their discovery is therefore often serendipitous.

Our research has led to two findings: that 4-DMAPy can direct the synthesis of low-silica SAPO-CHA in a low fluoride or fluoride-free medium and in the presence of colloidal SAPO-34 seeds; and, from parallel experiments, that without SAPO-34 seeds, use of the same directing agent under no- or low-fluoride , conditions unexpectedly led to the production of the present large pore aluminophosphate designated EMM-8.

Figure 1:
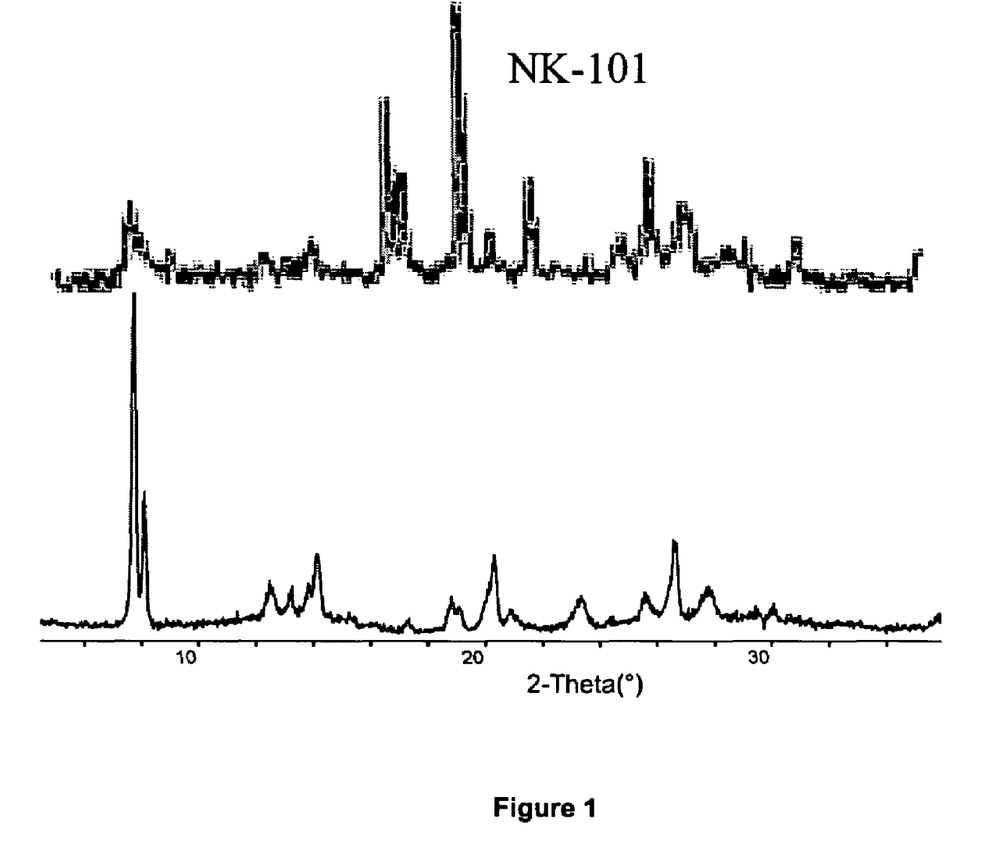
FIG. 1 is a comparison of the X-ray diffraction pattern of NK-101 with the X-ray diffraction pattern of Sample A in Example 1 after calcination as in Example 4. The ordinates for the two patterns are to the same scale and reflect intensity counts.

According to an article in the Chemical Journal of Chinese Universities, Vol. 22, No. 10, pages 192-195, dated October 2001, DMAPy has been used as a template in the synthesis of NK-101, an aluminophosphate. However, FIG. 1 provides a comparison of the X-ray diffraction pattern of NK-, 101 with that of EMM-8 and it is apparent from this comparison that the material of the invention is different from NK-101. In particular, in the X-ray diffraction pattern of NK-101, the most prominent diffraction peaks are at 2-theta values of approximately 17° and 19°, whereas these peaks are not present in the X-ray diffraction pattern of EMM-8.

In an article entitled "SSZ-51—A New Aluminophosphate Zeotype: Synthesis, Crystal Structure, NMR, and Dehydration Properties", published on the Web by the American Chemical Society on Jun. 23, 2004, Morris et al. report that they have synthesized and solved the structure of a new aluminophosphate zeotype framework structure, SSZ-5 1, having the empirical formula $Al_4(PO_4)_4.F.C_7N_2H_{11}.0.5H_2O$. The synthesis employs 4-dimethylaminopyridine , as a structure directing agent and requires the presence of fluoride ion as a mineralizing agent. The structure of SSZ-51 is said to be closely related to that of SAPO-40, an AFR framework type material, and to contain intersecting channels defined by 8- and 12-membered ring windows. It appears that SSZ-51 is isostructural with EMM-8.

U.S. Patent Application Publication No. 2003/0232718 published Dec. 18, 2003 discloses the synthesis of silicoaluminophosphate molecular sieves using templates that contain at least one dimethylamino moeity. The use of such templates is said to result in good quality SAPO molecular sieves of CHA framework type.

EP-A-0 324 082 discloses the synthesis of non-zeolite molecular sieves by contacting alumina or silica-alumina bodies with a liquid reaction mixture containing a reactive source of phosphorus and an organic templating agent.

SUMMARY

In one aspect, the invention resides in a crystalline molecular sieve having a framework comprising tetrahedrally coordinated atoms (T) connected by bridging atoms and having the coordination sequence and vertex symbols listed in Table 3 below.

In another aspect, the invention resides in a crystalline molecular sieve having, in its as-synthesized form, an X-ray diffraction pattern including the lines listed in Table 4 below. In its calcined form, the crystalline molecular sieve of the invention has an X-ray diffraction pattern including the lines listed in Table 5 below. The phrase "including the lines" as used herein means that peaks are expected to be present at or close to the lines indicated in the Tables, but not necessarily in the relative intensities specified, which can vary depending on a number of factors as discussed later.

In yet another aspect, the invention resides in a crystalline material having, in its as-synthesized form, an X-ray diffraction pattern including the lines listed in Table 4 below and represented, in its as-synthesized form and on an anhydrous basis, by the empirical formula:

$mR:F_a:(M_xAl_yP_z)O_2$ wherein R represents at least one directing agent, preferably 4-dimethylaminopyridine; , m is the number of moles of R per mole of $(M_xAl_yP_z)O_2$ and m has a value from 0 to 1, such as from 0.1 to about 0.5, for example from 0.1 to about 0.3; wherein a is the number of moles of fluoride ion (F) per mole of $(M_xAl_yP_z)O_2$ and a/y is less than 0.25 and preferably is 0; wherein x, y, and z represent the mole fraction of M, Al and P, as tetrahedral oxides; and wherein M is a metal selected from one of Groups 1 to 14 and Lanthanoids of the Periodic Table of Elements, and preferably M is selected from B, Co, Cr, Cu, Fe, Ga, Ge, Mg, Mn, Ni, Si, Sn, Ti, Zn and Zr. Most preferably, M is silicon. In one embodiment, x is from 0 to about 0.25, y is from about 0.3 to about 0.7 and z is from about 0.25 to about 0.7. In another embodiment, x is from 0 to about 0.15, y is from about 0.4 to about 0.6 and z is from about 0.3 to about 0.6. In yet another embodiment, x is from about 0 to about 0.12, y is from about 0.45 to about 0.55 and z is from about 0.35 to about 0.55. For ALPO molecular sieves, x is zero.

In still another aspect, the invention resides in a method of synthesizing the crystalline material of the invention, the process comprising: (a) forming a reaction mixture comprising water, a source of aluminum, a source of phosphorus, at least one structure directing agent comprising 4-dimethylaminopyridine, , optionally a source of metal M and optionally a source of fluoride ion, wherein F: $Al_2O_3$ molar ratio of said reaction mixture is preferably less than 0.5 and most preferably is 0; (b) inducing crystallization of said crystalline material from the reaction mixture; and (c) recovering said crystalline material from the reaction mixture.

In a further aspect, the invention resides in a method of synthesizing a crystalline material having the CHA framework type, the process comprising: (a) forming a reaction mixture comprising a source of aluminum, a source of phosphorus, optionally a source of metal M, at least one directing agent comprising 4-dimethylaminopyridine and seeds of a CHA framework type material, such as SAPO-34; (b) inducing crystallization of said crystalline material from the reaction mixture; and (c) recovering said crystalline material from the reaction mixture.

In still a further aspect, the invention resides in the use of the crystalline material of said one aspect of the invention as a sorbent and as a catalyst in organic conversion reactions.

DETAILED DESCRIPTION OF THE EMBODIMENTS

In one embodiment, the present invention relates to a porous crystalline material, EMM-8, and its synthesis in a low fluoride or fluoride-free medium with the organic directing agent, 4-dimethylaminopyridine. The crystalline structure remains intact after calcination to remove the directing agent and adsorption data indicate that the resultant material has large pores. In particular, the calcined material adsorbs a significant amount of mesitylene, as well as 2,2-dimethylbutane, n-hexane, and methanol. The invention also resides in the use of EMM-8 as a sorbent and as a catalyst in organic conversion reactions and to synthesis of CHA framework materials with the organic directing agent, 4-dimethylaminopyridine.

The EMM-8 of the invention is a porous crystalline material having a framework of tetrahedral atoms connected by bridging atoms, the tetrahedral atom framework being defined by the interconnections between the tetrahedrally coordinated atoms in its framework. As with any porous crystalline material, the structure of EMM-8 can be defined by the interconnections between the tetrahedrally coordinated atoms in its framework. In particular, EMM-8 has a framework of tetrahedral (T) atoms connected by bridging atoms, wherein the tetrahedral atom framework is defined by connecting the nearest tetrahedral (T) atoms in the manner shown in Table 1 below.

TABLE 1

| T atom | Connected to: |
|---|---|
| T1 | T2, T3, T4, T28 |
| T2 | T1, T3, T4, T14 |
| T3 | T1, T2, T7, T15 |
| T4 | T1, T2, T16, T25 |
| T5 | T6, T7, T8, T32 |
| T6 | T5, T7, T8, T10 |
| T7 | T3, T5, T6, T11 |
| T8 | T5, T6, T12, T29 |
| T9 | T10, T11, T12, T20 |
| T10 | T6, T9, T11, T12 |
| T11 | T7, T9, T10, T15 |
| T12 | T8, T9, T10, T17 |
| T13 | T14, T15, T16, T24 |
| T14 | T2, T13, T15, T16 |
| T15 | T3, T11, T13, T14 |
| T16 | T4, T13, T14, T21 |
| T17 | T12, T18, T19, T20 |
| T18 | T17, T19, T20, T30 |
| T19 | T17, T18, T23, T31 |
| T20 | T9, T17, T18, T32 |
| T21 | T16, T22, T23, T24 |
| T22 | T21, T23, T24, T26 |
| T23 | T19, T21, T22, T27 |
| T24 | T13, T21, T22, T28 |
| T25 | T4, T26, T27, T28 |
| T26 | T22, T25, T27, T28 |
| T27 | T23, T25, T26, T31 |
| T28 | T1, T24, T25, T26 |
| T29 | T8, T30, T31, T32 |
| T30 | T18, T29, T31, T32 |
| T31 | T19, T27, T29, T30 |
| T32 | T5, T20, T29, T30 |

Figure 9:
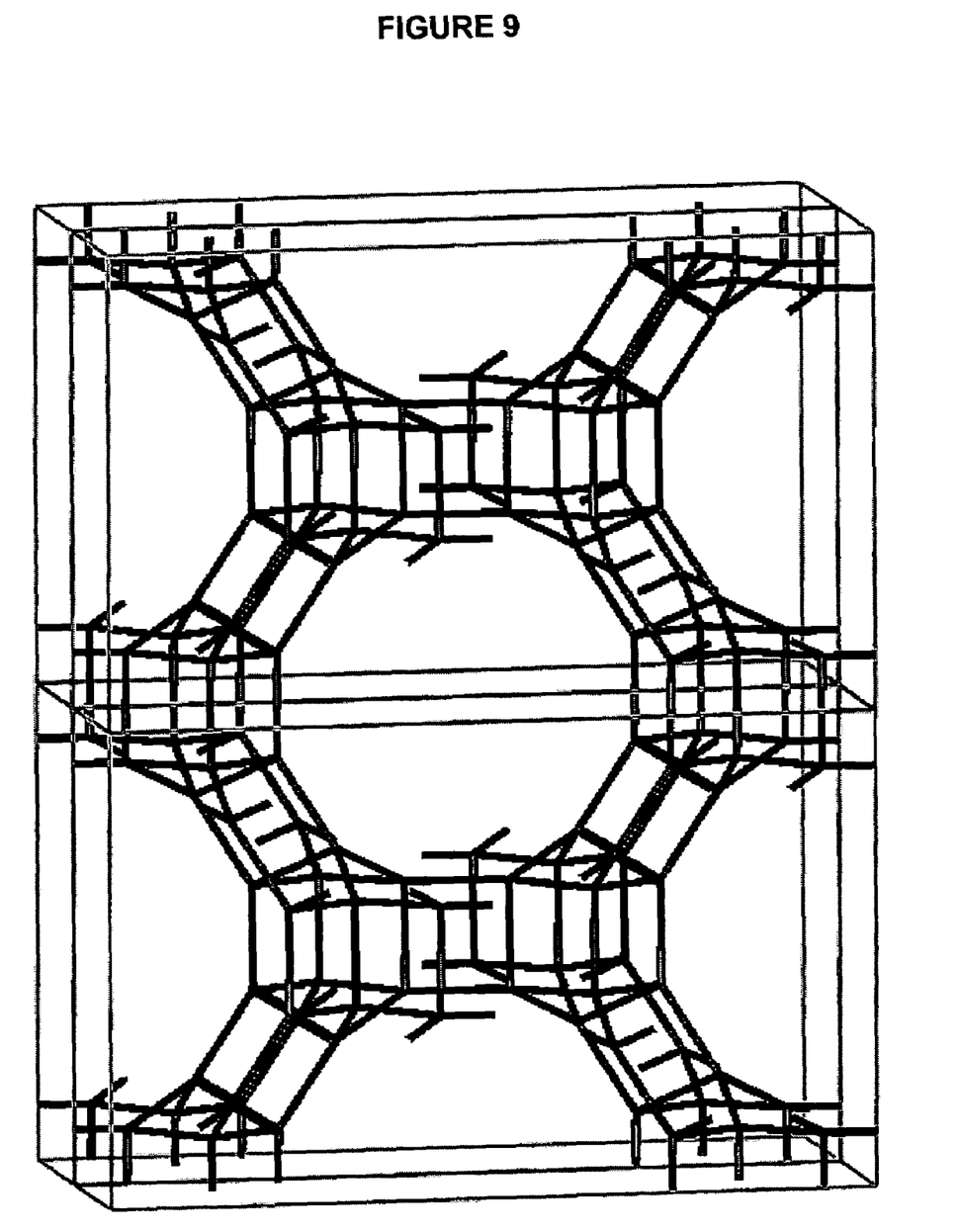
FIG. 9 is an illustration of the framework structure of EMM-8 showing only the tetrahedral atoms.

In addition to describing the structure of EMM-8 by the interconnections of the tetrahedral atoms as in Table 1 above, it may be defined by its unit cell, which is the smallest repeating unit containing all the structural elements of the material. The pore structure of EMM-8 is illustrated in FIG. 9 (which shows only the tetrahedral atoms) down the direction of the 12-member ring channel. There are four unit cell units in FIG. 9, whose limits are defined by four boxes. Table 2 lists the typical positions of each tetrahedral atom in the unit cell in units of Angstroms. Each tetrahedral atom is bonded to bridging atoms, which are also bonded to adjacent tetrahedral atoms. Tetrahedral atoms are those capable of having tetrahedral coordination, including one or more of, but not limiting, lithium, beryllium, boron, magnesium, aluminum, silicon, phosphorus, titanium, chromium, manganese, iron, cobalt, nickel, copper, zinc, zirconium, gallium, germanium, arsenic, indium, tin, and antimony. Bridging atoms are those capable of connecting two tetrahedral atoms, examples of which include, but are not limited to oxygen, nitrogen, fluorine, sulfur, selenium, and carbon atoms.

In the case of oxygen, it is also possible that the bridging oxygen is also connected to a hydrogen atom to form a hydroxyl group (—OH—). In the case of carbon it is also possible that the carbon is also connected to two hydrogen atoms to form a methylene group (—CH$_2$—). For example, bridging methylene groups have been seen in the zirconium diphosphonate, MIL-57. See: C. Serre, G. Férey, *J. Mater. Chem.* 12, p. 2367 (2002). Bridging sulfur and selenium atoms have been seen in the UCR-20-23 family of microporous materials. See: N. Zheng, X. Bu, B. Wang, P. Feng, *Science* 298, p. 2366 (2002). Bridging fluorine atoms have been seen in lithium hydrazinium fluoroberyllate, which has the ABW structure type. See: M. R. Anderson, I. D. Brown, S. Vilminot, *Acta Cryst.* B29, p. 2626 (1973). Since tetrahedral atoms may move about due to other crystal forces (presence of inorganic or organic species, for example), or by the choice of tetrahedral and bridging atoms, a range of ±0.1 nm (±1 Angstrom) is implied for the x and y coordinate positions and a range of ±0.05 nm (±0.5 Angstrom) for the z coordinate positions in Table 2.

TABLE 2

Positions of tetrahedral (T) atoms for the EMM-8 structure when T = silicon and the bridging atoms are oxygen.

| Atom | x(nm) | y(nm) | z(nm) |
|---|---|---|---|
| T1 | 0.2926 | 0.2757 | 0.5573 |
| T2 | 0.3234 | 0.1530 | 0.2716 |
| T3 | 0.1524 | 0.1588 | 0.0121 |
| T4 | 0.5757 | 0.1522 | 0.0821 |
| T5 | 1.8568 | 0.2757 | 0.1383 |
| T6 | 1.8260 | 0.1530 | 0.4240 |
| T7 | 1.9970 | 0.1588 | 0.6835 |
| T8 | 1.5738 | 0.1522 | 0.6135 |
| T9 | 1.8568 | 1.0975 | 0.1383 |
| T10 | 1.8260 | 1.2202 | 0.4240 |
| T11 | 1.9970 | 1.2144 | 0.6835 |
| T12 | 1.5738 | 1.2210 | 0.6135 |
| T13 | 0.2926 | 1.0975 | 0.5573 |
| T14 | 0.3234 | 1.2202 | 0.2716 |
| T15 | 0.1524 | 1.2144 | 0.0121 |
| T16 | 0.5757 | 1.2210 | 0.0821 |
| T17 | 1.4200 | 0.9623 | 0.5573 |
| T18 | 1.4508 | 0.8396 | 0.2716 |
| T19 | 1.2798 | 0.8454 | 0.0121 |
| T20 | 1.7031 | 0.8388 | 0.0821 |
| T21 | 0.7294 | 0.9623 | 0.1383 |
| T22 | 0.6986 | 0.8396 | 0.4240 |
| T23 | 0.8696 | 0.8454 | 0.6835 |
| T24 | 0.4464 | 0.8388 | 0.6135 |
| T25 | 0.7294 | 0.4109 | 0.1383 |
| T26 | 0.6986 | 0.5336 | 0.4240 |
| T27 | 0.8696 | 0.5278 | 0.6835 |
| T28 | 0.4464 | 0.5344 | 0.6135 |
| T29 | 1.4200 | 0.4109 | 0.5573 |
| T30 | 1.4508 | 0.5336 | 0.2716 |
| T31 | 1.2798 | 0.5278 | 0.0121 |
| T32 | 1.7031 | 0.5344 | 0.0821 |

The complete structure of EMM-8 is built by connecting multiple unit cells as defined above in a fully-connected three-dimensional framework. The tetrahedral atoms in one unit cell are connected to certain tetrahedral atoms in all of its adjacent unit cells. While Table 1 lists the connections of all the tetrahedral atoms for a given unit cell of EMM-8, the connections may not be to the particular atom in the same unit cell but to an adjacent unit cell. All of the connections listed in Table 1 are such that they are to the closest tetrahedral (T) atoms, regardless of whether they are in the same unit cell or in adjacent unit cells.

Although the Cartesian coordinates given in Table 2 above may accurately reflect the positions of tetrahedral atoms in an idealized structure, the true structure can be more accurately described by the connectivity between the framework atoms as shown in Table 1 above. Another way to describe this connectivity is by the use of coordination sequences as applied to microporous frameworks by W. M. Meier and H. J.

Moeck, in the *Journal of Solid State Chemistry* 27, p. 349 (1979). In a microporous framework, each tetrahedral atom, $N_0$, (T-atom) is connected to $N_1=4$ neighboring T-atoms through bridging atoms (typically oxygen). These neighboring T-atoms are then connected to $N_2$ T-atoms in the next shell. The $N_2$ atoms in the second shell are connected to $N_3$ T-atoms in the third shell, and so on. Each T-atom is only counted once, such that, for example, if a T-atom is in a 4-membered ring, at the fourth shell the $N_0$ atom is not counted a second time, and so on. Using this methodology, a coordination sequence can be determined for each unique T-atom of a 4-connected net of T-atoms. The following line lists the maximum number of T-atoms for each shell.

$$N_0=1 \ N_1 \leq 4 \ N_2 \leq 12 \ N_3 \leq 36 \ N_k \leq 4 \cdot 3^{k-1}$$

For a given T-atom in a 3-dimensional framework, there are six angles associated with the connections to its 4 neighboring T-atoms. A way of indicating the size of the smallest ring associated with each of these six angles, called the vertex symbol, was developed by M. O'Keeffe and S. T. Hyde in *Zeolites* 19, p. 370 (1997). The order is such that opposite pairs of angles are grouped together. The vertex symbol $4.4.6.6.6_2.8$, for example, indicates that the first pair of opposite angles contains 4-rings, the second pair contains 6-rings, and the third pair contains two 6-rings and an 8-ring. The Structure Commission of the International Zeolite Association recognize that the combination of coordination sequence and vertex symbol together appear unique for a particular framework topology such that they can be used to unambiguously distinguish microporous frameworks of different types (see "Atlas of Zeolite Framework Types", Ch. Baerlocher, W. M. Meier, D. H. Olson, Elsevier, Amsterdam (2001). One way to determine the coordination sequence and vertex symbol for a given structure is from the atomic coordinates of the framework atoms using the computer program zeoTsites (see G. Sastre, J. D. Gale, *Microporous and mesoporous Materials* 43, p. 27 (2001).

The coordination sequence and vertex symbols for the EMM-8 structure are given in Table 3. The T-atom connectivity as listed in Table 3 is for T-atoms only. Bridging atoms, such as oxygen usually connect the T-atoms. Although most of the T-atoms are connected to other T-atoms through bridging atoms, it is recognized that in a particular crystal of a material having a framework structure, it is possible that a number of T-atoms may not be connected to one another. Reasons for non-connectivity include, but are not limited by, T-atoms located at the edges of the crystals and by defect sites caused by, for example, vacancies in the crystal. The framework listed in Table 3 is not limited in any way by its composition, unit cell dimensions or space group symmetry.

While the idealized structure contains only 4-coordinate T-atoms, it is possible under certain conditions that some of the framework atoms may be 5- or, 6-coordinate. This may occur, for example, under conditions of hydration when the composition of the material contains mainly phosphorus and aluminum T-atoms. When this occurs it is found that T-atoms may be also coordinated to one or two oxygen atoms of water molecules ($-OH_2$), or of hydroxyl groups ($-OH$). For example, the molecular sieve $AlPO_4$-34 is known to reversibly change the coordination of some aluminum T-atoms from 4-coordinate to 5- and 6-coordinate upon hydration as described by A. Tuel et al. in *J. Phys. Chem. B* 104, p. 5697 (2000). It is also possible that some framework T-atoms can be coordinated to fluoride atoms ($-F$) when materials are prepared in the presence of fluorine to make materials with 5-coordinate T-atoms as described by H. Koller in *J. Am. Chem. Soc.* 121, p. 3368 (1999).

It may happen in some particular compositions that, because of a specific ordering of T-atoms, the actual unit cell may double in size to allow the specific ordering to occur. This is the case in the aluminophosphate and metalloaluminophosphate compositions of EMM-8 where there are alternating aluminum and phosphorus T-atoms. For example, the unit cell of the AlPO form of EMM-8 is actually twice the length along the z-axis as indicated in Table 2, such that there are 64 T-atoms in the unit cell.

In its as-synthesized form, EMM-8 typically has an X-ray diffraction pattern including the lines listed in Table 4 below:

TABLE 4

| 2-Theta | d, nm | Relative Intensity |
|---|---|---|
| 7.58 ± 0.05 | 1.164 ± 0.008 | M |
| 8.26 ± 0.05 | 1.069 ± 0.007 | M |
| 12.66 ± 0.05 | 0.698 ± 0.003 | S |
| 13.94 ± 0.05 | 0.634 ± 0.002 | S |
| 14.18 ± 0.05 | 0.623 ± 0.002 | VS |
| 18.94 ± 0.05 | 0.468 ± 0.001 | S |
| 19.18 ± 0.05 | 0.462 ± 0.001 | M |
| 19.60 ± 0.05 | 0.452 ± 0.001 | S |
| 25.48 ± 0.05 | 0.349 ± 0.001 | M |
| 25.62 ± 0.05 | 0.347 ± 0.001 | VS |
| 25.94 ± 0.05 | 0.343 ± 0.001 | VS |
| 26.12 ± 0.05 | 0.341 ± 0.001 | M |
| 28.08 ± 0.05 | 0.317 ± 0.001 | M |

In its as-calcined anhydrous form, EMM-8 is porous and has an X-ray, diffraction pattern including the lines listed in Table 5 below:

TABLE 5

| 2-Theta | d, nm | Relative Intensity |
|---|---|---|
| 7.54 ± 0.05 | 1.171 ± 0.008 | VS |
| 7.94 ± 0.05 | 1.112 ± 0.007 | M |

TABLE 3

| Atom Number | Atom Label | Coordination Sequence | | | | | | | | | Vertex |
|---|---|---|---|---|---|---|---|---|---|---|---|
| 1 | T1 | 4 | 10 | 17 | 28 | 46 | 63 | 86 | 117 | 142 | 168 | $4 \cdot 6 \cdot 4 \cdot 6 \cdot 6 \cdot 12$ |
| 2 | T2 | 4 | 9 | 16 | 27 | 44 | 65 | 87 | 110 | 138 | 171 | $4 \cdot 6 \cdot 4 \cdot 6_2 \cdot 4 \cdot 8$ |
| 3 | T3 | 4 | 9 | 18 | 30 | 43 | 64 | 90 | 111 | 139 | 178 | $4 \cdot 4 \cdot 4 \cdot 8 \cdot 6_3 \cdot 8$ |
| 4 | T4 | 4 | 9 | 18 | 29 | 42 | 65 | 91 | 111 | 138 | 176 | $4 \cdot 4 \cdot 4 \cdot 12 \cdot 6 \cdot 6_3$ |

TABLE 5-continued

| 2-Theta | d, nm | Relative Intensity |
| --- | --- | --- |
| 12.68 ± 0.05 | 0.697 ± 0.003 | W |
| 13.54 ± 0.05 | 0.653 ± 0.003 | W |
| 14.24 ± 0.05 | 0.621 ± 0.002 | M |
| 18.82 ± 0.05 | 0.471 ± 0.001 | W |
| 19.80 ± 0.05 | 0.448 ± 0.001 | W |
| 20.10 ± 0.05 | 0.441 ± 0.001 | W |
| 25.46 ± 0.05 | 0.349 ± 0.001 | W |
| 25.90 ± 0.05 | 0.344 ± 0.001 | W |
| 26.46 ± 0.05 | 0.336 ± 0.001 | W |

These, and all other X-ray diffraction data referred to herein, were collected with a Siemens D500 diffractometer with a voltage of 40 kV and a current of 30 mA using a copper target ($\lambda=0.154$ nm) and a curved graphite monochrometer. The diffraction data were recorded by step-scanning at 0.02 degrees of two-theta, where theta is the Bragg angle, and a counting time of 1 second for each step. The interplanar spacings, d's, were calculated in nanometres (nm), and the relative intensities of the lines, I/Io, where Io is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (75-100), s=strong (50-74), m=medium (25-49) and w=weak (0-24). It should be understood that diffraction data listed for this sample as single lines may consist of multiple overlapping lines which under certain conditions, such as differences in crystallite sizes or very high experimental resolution or crystallographic change, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history. In practice, therefore, at least some of the lines in the X-ray patterns of the crystalline material of the invention may exhibit significant variations in relative intensity from the values indicated in Tables 4 and 5.

To generate the as-calcined X-ray data listed in Table 5, about 0.5 grams of the dried, as-synthesized crystalline material are heated in an oven from room temperature under a flow of nitrogen at a rate of 10° C./minute to 400° C. and, while retaining the nitrogen flow, the sample is held at 400° C. for 30 minutes. The nitrogen flow is then ceased and air is passed over the sample while the temperature of the oven is raised at a rate of 10° C./minute to 600° C. The sample is then retained at 600° C. for 2 hours under air, whereafter the oven is cooled to room temperature to allow the XRD pattern to be recorded.

The XRD patterns of Tables 4 and 5 can be indexed to a monoclinic unit cell, in the space group C2/c (#15), having the following unit cell dimensions in mn:

As-synthesized: a=2.069, b=1.389, c=0.708, β=99.2°;

As-calcined: a=2.255, b=1.374, c=0.719, β=98.61°.

In a preferred embodiment, EMM-8 comprises at least [AlO$_4$] and [PO$_4$] corner sharing tetrahedral units and, in its as-synthesized, anhydrous form, is represented by the empirical formula:

mR:F$_a$:(M$_x$Al$_y$P$_z$)O$_2$ wherein R represents at least one directing agent, preferably an organic directing agent and most preferably 4-dimethylaminopyridine; m is the number of moles of R per mole of (M$_x$Al$_y$P$_z$)O$_2$ and m has a value from 0 to 1, such as from 0.1 to about 0.5, preferably from 0.1 to about 0.3; wherein F represents fluoride ion which may be present in the synthesis mixture, a is the number of moles of F per mole of (M$_x$Al$_y$P$_z$)O$_2$ and a/y is less than 0.25 and preferably is 0; wherein x, y, and z represent the mole fraction of M, Al and P as tetrahedral oxides; and wherein M is a metal selected from one of Groups 1 to 14 and Lanthanoids of the Periodic Table of Elements. Preferably M is selected from B, Co, Cr, Cu, Fe, Ga, Ge, Mg, Mn, Ni, Si, Sn, Ti, Zn and Zr. Most preferably, M is silicon.

In one embodiment, x is from 0 to about 0.25, y is from about 0.3 to about 0.7 and z is from about 0.25 to about 0.7. In another embodiment x is from about 0 to about 0.15, y is from about 0.4 to about 0.6 and z is from about 0.3 to about 0.6. In yet another embodiment x is from about 0 to about 0.12, y is from about 0.45 to about 0.55 and z is from about 0.35 to about 0.55. For ALPO molecular sieves, x is zero.

In its calcined form, the large pore (metallo) aluminophosphate of the present invention typically has an alpha value of at least 0.1, and more preferably at least 0.5, indicating that the material is useful as an acid catalyst in organic, and in particular hydrocarbon conversion reactions. The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

The crystalline (metallo)aluminophosphate material of the present invention can be produced from a synthesis mixture containing water, a source of phosphorus, a source of aluminum, optionally a source of metal M, such as silicon, optionally a source of fluoride ions and 4-dimethylaminopyridine (R). The synthesis mixture typically has a composition, expressed in terms of mole ratios of oxides, as follows:

| Component | Useful | Preferred |
| --- | --- | --- |
| P$_2$O$_5$:Al$_2$O$_3$ | 0.7 to 1.3 | 0.9 to 1.1 |
| SiO$_2$:Al$_2$O$_3$ | 0 to 0.9 | 0.05 to 0.5 |
| H$_2$O:Al$_2$O$_3$ | 10 to 100 | 20 to 50 |
| R:Al$_2$O$_3$ | 0.5 to 5.0 | 1.0 to 4.0 |
| F:Al$_2$O$_3$ | 0 to <0.75 | 0 to 0.5 |

A suitable source of phosphorus in the above mixture is phosphoric acid. Examples of suitable aluminum sources include hydrated aluminum oxides such as boehmite and pseudoboehmite. Suitable sources of silicon include silicates, e.g., fumed silica, such as Aerosil and Cabosil, tetraalkyl orthosilicates, and aqueous colloidal suspensions of silica, for example that sold by E.I. du Pont de Nemours under the tradename Ludox.

If present, the source of fluoride ions may be any compound capable of releasing fluoride ions in the synthesis mixture. Non-limiting examples of such sources of fluoride ions include salts containing one or several fluoride ions, such as metal fluorides, preferably, sodium fluoride, potassium fluoride, calcium fluoride, magnesium fluoride, strontium fluoride, barium fluoride, ammonium fluoride, tetraalkylammonium fluorides, such as tetramethylammonium fluoride, tetraethylammonium fluoride, hydrogen fluoride, and mixtures thereof. The preferred source of fluoride is hydrogen fluoride but, more preferably, the synthesis is conducted in the absence of added fluoride, that is with the F:$Al_2O_3$ molar ratio being zero.

Crystallization is carried out under either stirred or static conditions, preferably stirred conditions, at a temperature between about 100° C. and about 250° C., typically between about 150° C. and about 200° C., preferably between about 155° C. and about 180° C. Preferably, crystallization is conducted for about 2 to about 150 hours, preferably about 20 to about 100 hours, whereafter the resultant crystalline material is separated from the mother liquor and recovered, such as by centrifugation or filtration. The separated product can also be washed, recovered by centrifugation or filtration and dried. The crystalline product is typically in the form of platelets having a $d_{50}$ (50% by volume of crystals is smaller than the $d_{50}$ value) particle size less than 1 μm.

Synthesis of the large pore (metallo)aluminophosphate material of the invention may be facilitated by the presence of at least 0.1 ppm, such as at least 10 ppm, for example at least 100 ppm, conveniently at least 500 ppm of seed crystals from a previous synthesis based on total weight of the reaction mixture. It is, however, found that where seed crystals of a CHA framework-type molecular sieve, such as SAPO-34, are added to the synthesis mixture, the resultant product is a CHA framework-type molecular sieve rather than the large pore (metallo)aluminophosphate material of the invention.

As a result of the crystallization process, the recovered crystalline product contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C., typically in the presence of an oxygen-containing gas. This type of process can be used for partial or complete removal of the organic directing agent from the intracrystalline pore system.

Once the crystalline material of the invention has been synthesized, it can be formulated into a catalyst composition by combination with other materials, such as binders and/or matrix materials, that provide additional hardness or catalytic activity to the finished catalyst.

Materials which can be blended with the crystalline material of the invention can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of crystalline material contained in the final catalyst product ranges from 10 to 90 weight percent of the total catalyst, preferably 20 to 80 weight percent of the total catalyst.

The large pore crystalline material described herein can be used to dry gases and liquids; for selective molecular separation based on size and polar properties; as an ion-exchanger; as a catalyst in organic conversion reactions, such as cracking, hydrocracking, disproportionation, alkylation, isomerization, oxidation and synthesis of monoalkylamines and dialkylamines; as a chemical carrier; in gas chromatography; and in the petroleum industry to remove normal paraffins from distillates. Where the synthesis method of the invention produces a CHA framework-type molecular sieve, such a product would have similar uses and in particular would be useful as a catalyst in the conversion of oxygenates, such as methanol, to olefins, such as ethylene and propylene.

In order to more fully illustrate the nature of the invention and the manner of practising same, the following examples are presented.

EXAMPLE 1

The following ingredients were mixed, in sequence, and blended into a uniform gel using a microhomogenizer (Tissue Tearor Model 98730, available from Biospec Products, Inc, USA): 85 wt % $H_3PO_4$ (obtained from Aldrich Chemical Company), deionized $H_2O$, Catapal™ A (73.9 wt % $Al_2O_3$, available from CONDEA Vista Company, Texas, USA), and then 4-dimethylaminopyridine , (4-DMAPy) (obtained from Aldrich Chemical Company, USA). The molar ratio of the ingredients was as follows:

2.0 DMAPy:1.0 $Al_2O_3$:1.0 $P_2O_5$:40 $H_2O$

Figure 2:
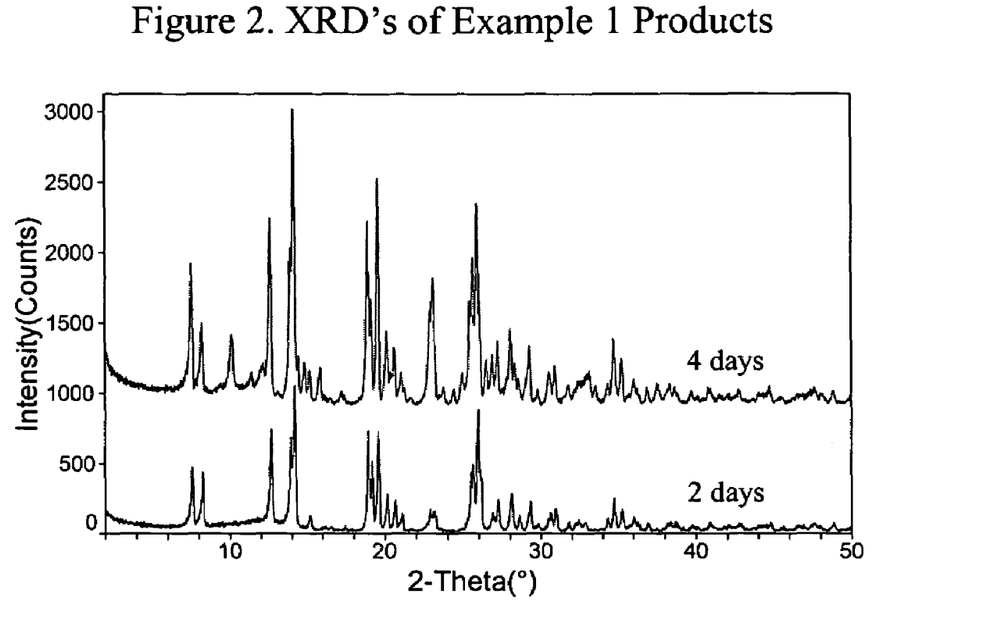
FIG. 2 gives the X-ray diffraction patterns of the as-synthesized products of Example 1 after crystallization for 2 days and 4 days.

The gel was then placed into a Parr bomb with Teflon liner, and was heated to 170° C. for 2 to 4 days while the bomb was tumbled at 40 rpm. The solid product was centrifuged and washed five times with deionized water, and was then dried in a 60° C. vacuum oven overnight. X-ray powder patterns of the product showed, in FIG. 2, that a crystalline product was obtained after two days of crystallization (Sample A). After four days of crystallization, additional diffraction peaks corresponding to an unidentified impurity appeared.

Figure 4:
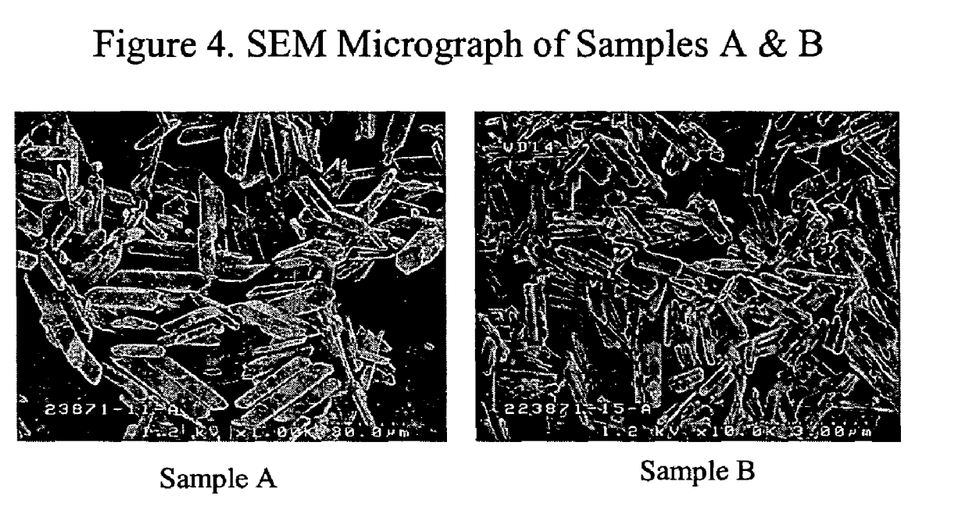
FIG. 4 gives scanning electron micrographs of Sample A of Example 1 and Sample B of Example 2.

Solid product yield of Sample A was 13.2%, based on the total weight of the starting gel. Elemental analysis gave the following results: Al, 16.0%; P, 17.9%. These results correspond to $Al_{1.0}P_{0.975}$ in composition and 71.2% for calculated total oxides. The residual weight was separately determined with TGA (Thermal Gravimetric Analysis) to be 72.6%. Sample A gave the scanning electron micrograph shown in FIG. 4 and had an XRD pattern with the peaks listed Table 6 below.

TABLE 6

| 2θ | d, nm | I % |
|---|---|---|
| 7.58 | 1.165 | 40 |
| 8.26 | 1.070 | 34 |
| 12.66 | 0.699 | 64 |
| 13.94 | 0.635 | 55 |
| 14.18 | 0.624 | 100 |
| 15.18 | 0.583 | 8 |
| 18.94 | 0.468 | 68 |
| 19.18 | 0.462 | 49 |
| 19.60 | 0.453 | 66 |
| 20.16 | 0.440 | 22 |
| 20.64 | 0.430 | 21 |
| 22.88 | 0.388 | 15 |
| 23.14 | 0.384 | 12 |
| 25.19 | 0.353 | 6 |
| 25.48 | 0.349 | 37 |
| 25.62 | 0.347 | 46 |
| 25.94 | 0.343 | 86 |
| 26.12 | 0.341 | 39 |
| 26.88 | 0.331 | 11 |
| 27.24 | 0.327 | 21 |
| 28.08 | 0.318 | 26 |
| 28.60 | 0.312 | 9 |
| 29.18 | 0.306 | 9 |
| 29.32 | 0.304 | 19 |
| 30.48 | 0.293 | 8 |
| 30.64 | 0.292 | 12 |

TABLE 6-continued

| 2θ | d, nm | I % |
|---|---|---|
| 30.98 | 0.288 | 14 |
| 32.42 | 0.276 | 7 |
| 34.32 | 0.261 | 8 |
| 34.72 | 0.258 | 22 |
| 35.24 | 0.254 | 12 |
| 36.04 | 0.249 | 8 |

The powder pattern of Sample A was indexed successfully in a monoclinic unit cell, in the Space Group C2/c (#15). The unit cell dimensions in nm are a=2.069, b=1.389, c=0.708, β=99.2°.

EXAMPLE 2

The procedure was identical to Example 1, except that hydrofluoric acid was added as the last ingredient and the ingredient ratio was the following:

0.5HF:2.0DMAPy:1.0Al$_2$O$_3$:1.0P$_2$O$_5$:40H$_2$O

Figure 3:
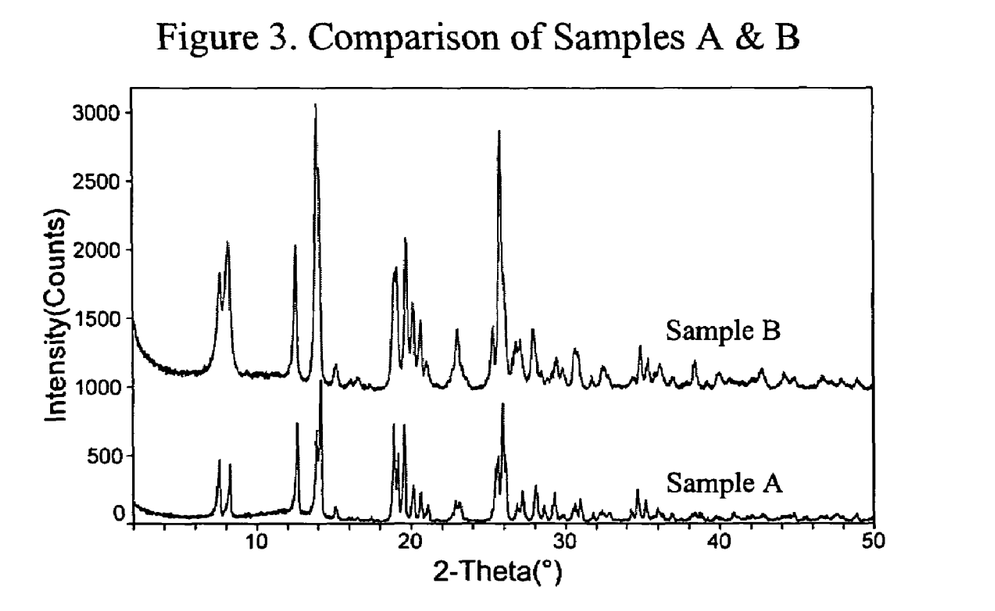
FIG. 3 compares the X-ray diffraction pattern of Sample A of Example 1 with that of Sample B of Example 2.

The crystallization was carried out for three days at 180° C. statically. The product yield was 12.9 wt %. The XRD pattern of the product (Sample B) is shown in FIG. 3 along with that of Sample A. The former is nearly identical to that of Sample A, although the peak width and relative intensity are somewhat different. The relative peak intensity difference is expected with the presence of F in Sample B. The broader peaks of Sample B are possibly due to the small platelet (<0.1 μm) morphology of the crystals as shown by a Scanning Electron Microscope micrograph (see FIG. 4).

The fact that the same crystalline product was obtained with different starting synthesis compositions (Examples 1 and 2), and that the XRD patterns of the products can be indexed establish that a pure phase material has been synthesized. The as-synthesized material has a unique XRD pattern.

EXAMPLE 3

The procedure of Example 1 was repeated to produce two additional samples, Samples C and D, except that Cabosil™ silica was added to each synthesis mixture after the Catapal™ alumina and before 4-dimethylaminopyridine. , The ingredient molar ratios were as follows:

2.0DMAPy:1.0Al$_2$O$_3$:(0.1 & 0.3)SiO$_2$:1.0P$_2$O$_5$:40H$_2$O

Figure 5:
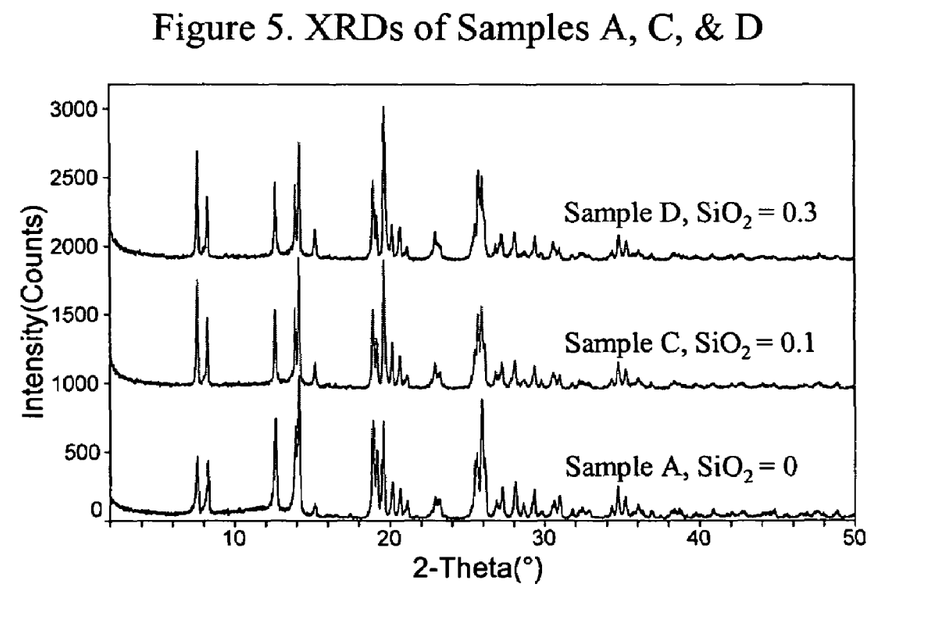
FIG. 5 is a comparison of the X-ray diffraction patterns of Sample A of Example 1 and Samples C and D of Example 3.

To the synthesis gel 0.15wt % Sample B was added as seeds. The crystallization was carried out for two days at 170° C. with tumbling at 40 rpm. The product yield was 18.9 and 19.6 wt %, for 0.1 SiO$_2$ and 0.3 SiO$_2$, respectively. The XRD patterns of the products (Samples C and D for 0.1 and 0.3 SiO$_2$, respectively) are shown in FIG. 5 along with that of Sample A. This Figure, along with the elemental analysis results below, shows that silicon atoms can be incorporated into the framework of Sample A.

Elemental analysis results were as follows: Sample C: Al=16.1%; P=16.9%; Si=2.38%. This corresponds to Al$_{1.0}$Si$_{0.058}$P$_{0.914}$ in composition and 71.2% for calculated total oxides. Sample D: Al=14.8%; P=15.7%; Si=2.38%. This corresponds to Al$_{1.0}$Si$_{0.154}$P$_{0.924}$ in composition and 69.1% for calculated total oxides.

The powder pattern of Sample C was indexed successfully in the same monoclinic unit cell as Sample A, in the Space Group C2/c(#15). The unit cell dimensions in nm are: a=2.169, b=1.386, c=0.705, β=98.9°. The unit cell volume is 2.0983 nm$^3$. These unit cell parameters are similar to those of Sample A.

EXAMPLE 4

Figure 6:
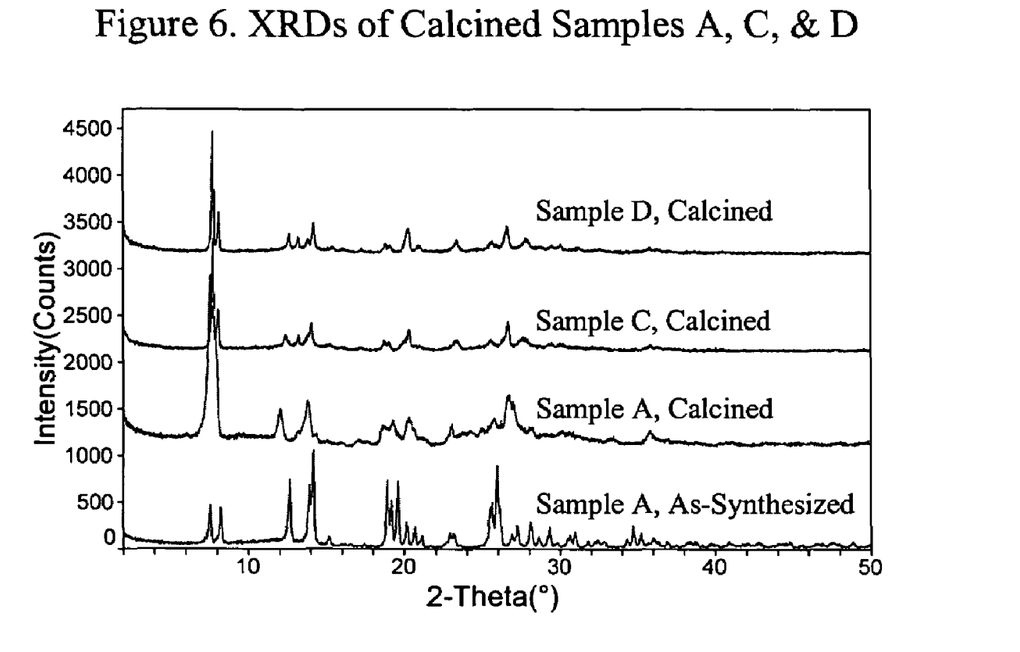
FIG. 6 is a comparison of the X-ray diffraction pattern of Sample A, as-synthesized, with the X-ray diffraction patterns of Samples A, C and D after calcination as in Example 4.

Calcination of the samples A, C and D (10° C./min to 400° C. in nitrogen, then dwell for 30 minutes in nitrogen before ramping to 600° C. at 10° C./min in air, and finally dwell at 600° C. for 2 hours in air) resulted in white crystalline products with the organic directing agent removed. The XRD patterns of the calcined samples, taken in ambient air so there may be some degree of rehydration, are shown in FIG. 6, along with that of the as-synthesized Sample A.

All three samples gave different XRD patterns from their as-synthesized counterparts. The calcined Sample A, being an AlPO$_4$, shows a different pattern from those of the calcined Samples C and D. The latter two, both being SAPOs, have similar XRD patterns. A similar phenomenon has been found in AlPO$_4$ and SAPOs having the CHA framework type. AlPO$_4$-34, for example, adopts a triclinic unit cell when exposed to moisture, whereas SAPO-34s having sufficiently high Si levels retain their rhombohedral symmetry after rehydration.

The XRD pattern of calcined Sample C was indexed in a monoclinic unit cell similar to that for the as-synthesized sample. The unit cell constants in nm are a=2.233, b=1.336, c=0.716, β=99.88°. The unit cell volume is 2.1050 nm$^3$. These unit cell parameters are very similar to those of as-synthesized , Sample C, with only about 0.3% increase in unit cell volume upon calcination.

EXAMPLE 5

Calcination of Sample C was conducted and XRDs were taken on a platinum sample stage that was enclosed in a chamber equipped with different sources of inert and reactive gases. The platinum sample stage also served as an XRD sample holder so that XRD patterns could be taken at different temperatures as well as under different atmospheres. First a pattern was taken on the as-synthesized , Sample C. Then, after a ramp in temperature at 10° C./min to 600° C. and dwelling at the temperature for two hours under a flow of dry air (15 ppm moisture), and cooling to 200° C., a second XRD pattern was taken. The flowing gas was switched to N$_2$ and the sample was cooled to room temperature before a third XRD pattern was taken in N$_2$. Afterwards the chamber was opened to the ambient air, which had a relative humidity of 82% (22° C.), for 16 hours, to ensure that the sample was fully hydrated. A fourth XRD pattern was then taken. Finally, the chamber was closed again, and the temperature was raised to 200° C. under N$_2$ to dehydrate the sample. A final fifth XRD pattern was taken at 200° C. in N$_2$.

Figure 7:
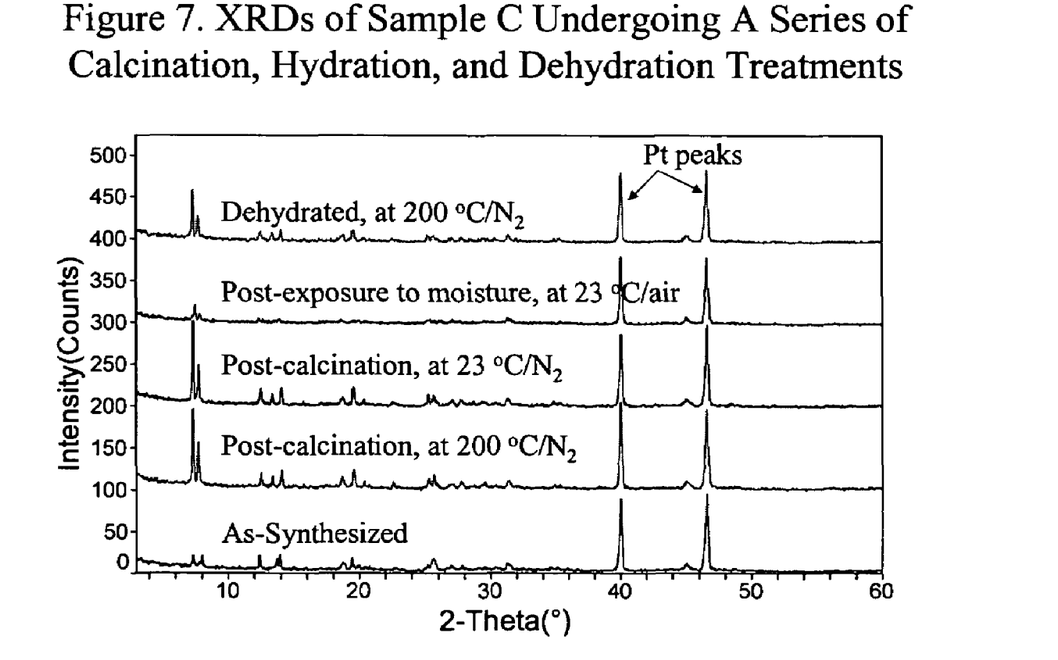
FIG. 7 gives the X-ray diffraction patterns of Sample C as-synthesized , and after undergoing a series of calcination, hydration and dehydration treatments as described in Example 5.

The results are shown in FIG. 7 and indicate that calcination results in some change in the XRD pattern as well as an increase in the overall diffraction intensity. Exposure to moisture reduces the diffraction intensity to the pre-calcination level, and the XRD pattern is again slightly changed. Then dehydration of the hydrated sample leads to an XRD pattern identical to that of the post-calcination sample, indicating the hydration process is at least partially reversible.

EXAMPLE 6

Calcined (600° C. for two hours) and degassed (at 500° C.) Sample A was exposed to different adsorbate molecules under specified conditions as listed in Table 7 below in a Thermal Gravimetric Analysis (TGA) unit. In all cases complete adsorption was attained. The diffusivity number $D/r^2$ given in Table 7 was obtained by analyzing the initial portion of the adsorption uptake curve. In all cases adsorption was found to be too fast for accurate determination of diffusivity. Therefore the numbers reported are the best estimates. Table 7 also provides, for comparison purposes, some adsorption data for the 10×10×9 ring material ITQ-13.

TABLE 7

| Adsorbate | Methanol | n-Hexane | 2,2-Dimethylbutane | Mesitylene |
|---|---|---|---|---|
| Sample A | | | | |
| Ads. Conditions | 35° C., 203 torr | 90° C., 75 torr | 120° C., 90 torr | 100° C., 2 torr |
| Ads. Capacity, wt % | 20.1 | 9.61 | 7.44 | 11.02 |
| $D/r^2$, sec$^{-1}$ | 0.066 | | 0.1 | 0.01 |
| ITQ-13 (For Comparison) | | | | |
| Ads. Capacity, wt % | | 7.60 | 5.40 | 0 |
| $D/r^2$, sec$^{-1}$ | | | 0.1 | |

The significant amount of mesitylene adsorption indicates that the new material has pore openings larger or equal to 0.7 nm (7 Å)(12-ring), and the large adsorption capacity suggests that the framework is very open.

EXAMPLE 7

Samples C and D, having Si/Al ratio of 0.058 and 0.154, respectively, were calcined at 600° C. for 2 hours before n-hexane cracking test was conducted. The standard α-test conditions (538° C.) were used. The α-numbers for these two samples were determined to be 9.1 and 23.3, respectively. These values show that the new material has potential for hydrocarbon conversion applications.

EXAMPLE 8

The synthesis procedure was identical to Example 1, except that Cabosil™ was added after Catapal™ and before 4-dimethylaminopyridine, and 100 ppm colloidal SAPO-34 seeds were added as the last ingredient. The ingredient ratio was as follows:

2.0DMAPy:1.0Al$_2$O$_3$:0.3SiO$_2$:1.0P$_2$O$_5$:40H$_2$O

Crystallization was carried out for two and four days at 170° C. with tumbling at 40 rpm. The solid yields for two and four days of crystallization were 17.85% and 21.07%, respectively.

Figure 8:
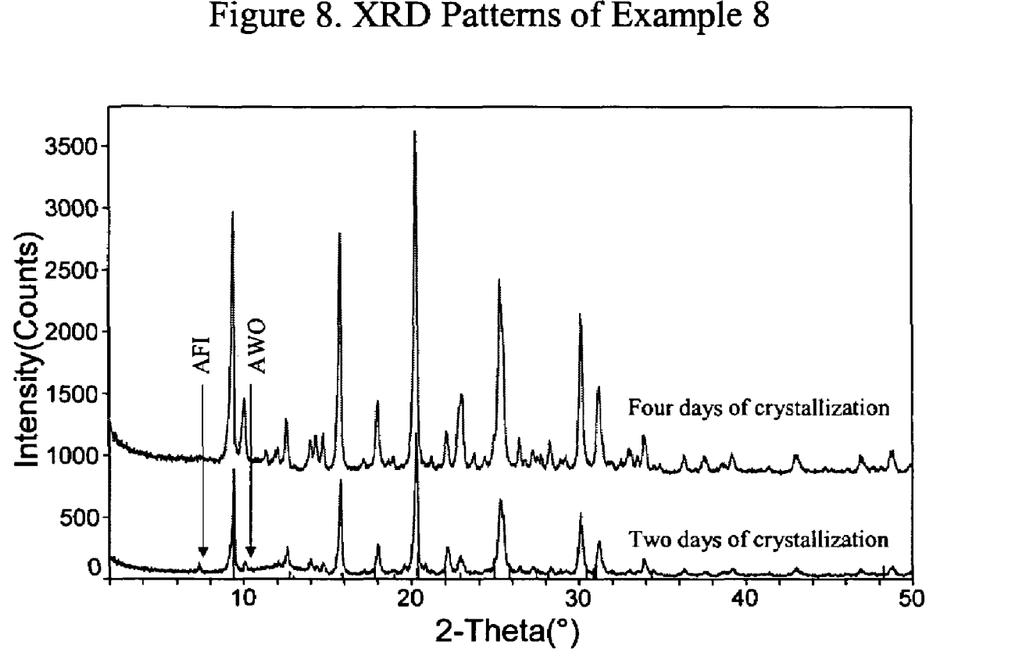
FIG. 8 gives the X-ray diffraction patterns of the as-synthesized products of Example 8 after crystallization for 2 days and 4 days.

The XRD patterns are shown in FIG. 8, which shows that SAPO-34 has been made, although impurities were present. The product of two-day crystallization had trace amount of AFI (AlPO$_4$-5) and what appeared to be AWO AlPO$_4$-21), while that of four-day crystallization had no AFI but an increased of AWO.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A crystalline molecular sieve having a framework comprising tetrahedrally coordinated atoms (T) connected by bridging atoms and having the coordination sequence and vertex symbols listed in the following table:

| Atom Number Symbol | Atom Label | Coordination Sequence | Vertex |
|---|---|---|---|
| 1 | T1 | 4 10 17 28 46 63 86 117 142 168 | 4·6·4·6·6·12 |
| 2 | T2 | 4 9 16 27 44 65 87 110 138 171 | 4·6·4·6$_2$·4·8 |
| 3 | T3 | 4 9 18 30 43 64 90 111 139 178 | 4·4·4·8·6$_3$·8 |
| 4 | T4 | 4 9 18 29 42 65 91 111 138 176 | 4·4·4·12·6·6$_3$. |

2. A crystalline molecular sieve having, in its as-synthesized form, an X-ray diffraction pattern including the lines listed in the following table:

| 2-Theta | d, nm | Relative Intensity |
|---|---|---|
| 7.58 ± 0.05 | 1.164 ± 0.008 | M |
| 8.26 ± 0.05 | 1.069 ± 0.007 | M |
| 12.66 ± 0.05 | 0.698 ± 0.003 | S |
| 13.94 ± 0.05 | 0.634 ± 0.002 | S |
| 14.18 ± 0.05 | 0.623 ± 0.002 | VS |
| 18.94 ± 0.05 | 0.468 ± 0.001 | S |
| 19.18 ± 0.05 | 0.462 ± 0.001 | M |
| 19.60 ± 0.05 | 0.452 ± 0.001 | S |
| 25.48 ± 0.05 | 0.349 ± 0.001 | M |
| 25.62 ± 0.05 | 0.347 ± 0.001 | VS |
| 25.94 ± 0.05 | 0.343 ± 0.001 | VS |
| 26.12 ± 0.05 | 0.341 ± 0.001 | M |
| 28.08 ± 0.05 | 0.317 ± 0.001 | M. |

3. A crystalline molecular sieve having, in its calcined form, an X-ray diffraction pattern including the lines listed in the following table:

| 2-Theta | d, nm | Relative Intensity |
|---|---|---|
| 7.54 ± 0.05 | 1.171 ± 0.008 | VS |
| 7.94 ± 0.05 | 1.112 ± 0.007 | M |
| 12.68 ± 0.05 | 0.697 ± 0.003 | W |
| 13.54 ± 0.05 | 0.653 ± 0.003 | W |
| 14.24 ± 0.05 | 0.621 ± 0.002 | M |
| 18.82 ± 0.05 | 0.471 ± 0.001 | W |
| 19.80 ± 0.05 | 0.448 ± 0.001 | W |
| 20.10 ± 0.05 | 0.441 ± 0.001 | W |
| 25.46 ± 0.05 | 0.349 ± 0.001 | W |
| 25.90 ± 0.05 | 0.344 ± 0.001 | W |
| 26.46 ± 0.05 | 0.336 ± 0.001 | W. |

4. The crystalline molecular sieve of claim 3, further comprising [AlO$_4$] and [PO$_4$] corner sharing tetrahedral units.

5. A crystalline material comprising [AlO$_4$] and [PO$_4$] corner sharing tetrahedral units and having an X-ray diffraction pattern including the lines listed in the following table:

| 2-Theta | d, nm | Relative Intensity |
|---|---|---|
| 7.58 ± 0.05 | 1.164 ± 0.008 | M |
| 8.26 ± 0.05 | 1.069 ± 0.007 | M |

-continued

| 2-Theta | d, nm | Relative Intensity |
|---|---|---|
| 12.66 ± 0.05 | 0.698 ± 0.003 | S |
| 13.94 ± 0.05 | 0.634 ± 0.002 | S |
| 14.18 ± 0.05 | 0.623 ± 0.002 | VS |
| 18.94 ± 0.05 | 0.468 ± 0.001 | S |
| 19.18 ± 0.05 | 0.462 ± 0.001 | M |
| 19.60 ± 0.05 | 0.452 ± 0.001 | S |
| 25.48 ± 0.05 | 0.349 ± 0.001 | M |
| 25.62 ± 0.05 | 0.347 ± 0.001 | VS |
| 25.94 ± 0.05 | 0.343 ± 0.001 | VS |
| 26.12 ± 0.05 | 0.341 ± 0.001 | M |
| 28.08 ± 0.05 | 0.317 ± 0.001 | M. |

6. The crystalline material of claim 5 and also comprising [SiO$_4$] corner sharing tetrahedral units.

7. The crystalline material of claim 5 and represented by the empirical formula, on an anhydrous basis:

$$mR:F_a:(M_xAl_yP_z)O_2$$

wherein R represents at least one directing agent; wherein m is the number of moles of R per mole of $(M_xAl_yP_z)O_2$; wherein a is the number of moles of fluoride ion (F) per mole of $(M_xAl_yP_z)O_2$; wherein x, y, and z represent the mole fraction of M, Al and P as tetrahedral oxides; and wherein M is a metal selected from one of Groups 1 to 14 and Lanthanoids of the Periodic Table of Elements.

8. The crystalline material of claim 7 wherein m has a value from 0 to about 1.

9. The crystalline material of claim 7 wherein m has a value from about 0.1 to about 0.5.

10. The crystalline material of claim 7 wherein R is 4-dimethylaminopyridine.

11. The crystalline material of claim 7 wherein a/y is less than 0.25.

12. The crystalline material of claim 7 wherein a/y is 0.

13. The crystalline material of claim 7 wherein M is selected from one of the group consisting of B, Co, Cr, Cu, Fe, Ga, Ge, Mg, Mn, Ni, Sn, Ti, Zn and Zr.

14. The crystalline material of claim 7 wherein M is silicon.

15. The crystalline material of claim 7 wherein x is from 0 to about 0.25, y is from about 0.3 to about 0.7 and z is from about 0.25 to about 0.7.

16. The crystalline material of claim 7 wherein x is from about 0 to about 0.15, y is from about 0.4 to about 0.6 and z is from about 0.3 to about 0.6.

17. A method of synthesizing the crystalline material of claim 5, the process comprising: (a) forming a reaction mixture comprising water; a source of aluminum, a source of phosphorus, optionally a source of metal other than aluminum, optionally a source of fluoride ions, and at least one directing agent comprising 4-dimethylaminopyridine, (R); (b) inducing crystallization of said crystalline material from the reaction mixture; and (c) recovering said crystalline material from the reaction mixture.

18. The method of claim 17 wherein the reaction mixture has a composition, in terms of mole ratios, within the following ranges:
P$_2$O$_5$:Al$_2$O$_3$=0.7 to 1.3
SiO$_2$:Al$_2$O$_3$=0 to 0.9
H$_2$O:Al$_2$O$_3$=10 to 100
R:Al$_2$O$_3$=0.5 to 5.0
F:Al$_2$O$_3$=0 to <0.75.

19. The method of claim 18 wherein F:Al$_2$O$_3$ is zero.

20. The method of claim 17 wherein the reaction mixture has a composition, in terms of mole ratios, within the following ranges:
P$_2$O$_5$:Al$_2$O$_3$=0.9 to 1.1
SiO$_2$:Al$_2$O$_3$=0.05 to 0.5
H$_2$O:Al$_2$O$_3$=20 to 50
R:Al$_2$O$_3$=1.0 to 4.0
F:Al$_2$O$_3$=0 to 0.5.

21. The method of claim 20 wherein F:Al$_2$O$_3$ is zero.

22. The method of claim 17, wherein crystallization of said crystalline material is conducted at a temperature of about 100° C. to about 250° C.

23. The method of claim 17, wherein crystallization of said crystalline material is conducted at a temperature of about 130° C. to about 200° C.

24. A hydrocarbon conversion process comprising contacting a hydrocarbon feedstock with a catalyst comprising a crystalline material produced by the method of claim 17.

25. A hydrocarbon conversion process comprising contacting a hydrocarbon feedstock with a catalyst comprising the porous crystalline material of claim 5.

26. A method of synthesizing a crystalline material having the CHA framework type, the process comprising:(a) forming a reaction mixture comprising a source of aluminum, a source of metal other than aluminum, a source of phosphorus, at least one directing agent comprising 4-dimethylaminopyridine and seeds of a CHA framework type material, such as SAPO-34; (b) inducing crystallization of said crystalline material from the reaction mixture; and (c) recovering said crystalline material from the reaction mixture.

27. A process for converting an oxygenate-containing feedstock to olefins comprising contacting the feedstock with a catalyst comprising a porous crystalline material produced by the method of claim 26.

* * * * *